United States Patent [19]

Grigoleit et al.

[11] 4,098,838
[45] Jul. 4, 1978

[54] PROCESS FOR OBTAINING SULFUR FREE PURE NAPHTHALENE FROM BITUMINOUS COAL TAR AND THIONAPHTHENE AS A BY-PRODUCT

[75] Inventors: Georg Grigoleit, Dorsten, Rhade; Helmut Köhler, Duisburg, Gerd Collin; Kurt Matern, both of Duisburg-Meiderich, all of Fed. Rep. of Germany

[73] Assignee: Rütgerswerke Aktiengesellschaft, Frankfurt am Main, Germany

[21] Appl. No.: 711,678

[22] Filed: Aug. 4, 1976

[30] Foreign Application Priority Data

Aug. 7, 1975 [DE] Fed. Rep. of Germany ....... 2535192

[51] Int. Cl.² .................... C07C 7/01; C07D 333/52
[52] U.S. Cl. ........................ 260/674 N; 260/330.5
[58] Field of Search ................... 260/674 N, 330.5

[56] References Cited

U.S. PATENT DOCUMENTS

| 1,996,262 | 4/1935 | Todd et al. | 260/674 N |
| 2,920,121 | 1/1960 | Sisco et al. | 260/674 N |
| 2,955,144 | 10/1960 | Sisco et al. | 260/674 N |
| 3,511,889 | 5/1970 | Vorozhtsov et al. | 260/674 N |

FOREIGN PATENT DOCUMENTS 1,261,843  2/1968  Fed. Rep. of Germany ... 260/674 N

Primary Examiner—Delbert E. Gantz
Assistant Examiner—C. E. Spresser
Attorney, Agent, or Firm—Beveridge, DeGrandi, Kline & Lunsford

[57] ABSTRACT

In a process for obtaining substantially sulfur free pure naphthalene from bituminous coal tar and thionaphthene as a by-product, a de-phenolized thionaphthene-containing naphthalene fraction from oxidative purification is extracted with concentrated sulfuric acid and acetic acid anhydride in benzene. The thionaphthene is converted into its sulfonic acid derivative and water washed from the benzene-naphthalene mixture. The benzene is distilled leaving pure naphthalene. The sulfonic acid group is cleaved from the thionaphthene with superheated steam to yield thionaphthene.

5 Claims, 1 Drawing Figure

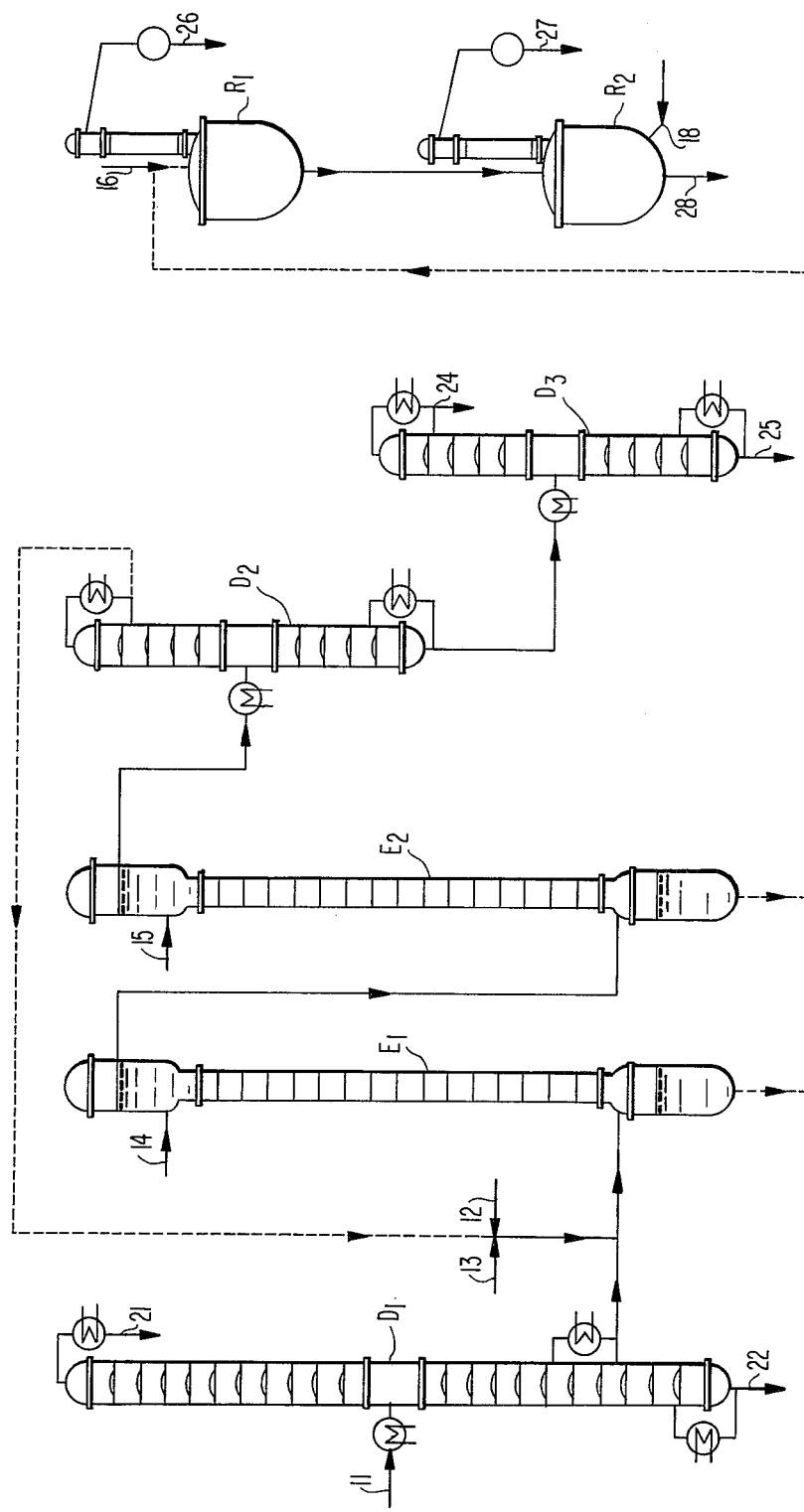

PROCESS FOR OBTAINING SULFUR FREE PURE NAPHTHALENE FROM BITUMINOUS COAL TAR AND THIONAPHTHENE AS A BY-PRODUCT

The invention relates to a process for obtaining substantially sulfur free pure naphthalene. Substantially pure thionaphthene (benzothiophene) is isolated as a by-product of the process.

Chemical engineering previously derived sulfur free naphthalene from bituminous coal tar either by treatment of the naphthalene with metallic sodium in the melt, or by treatment with sulfuric acid and formaldehyde at an elevated temperature. Metallic sodium and sulfuric acid processes lead to the wasteful destruction of thionaphthene (benzothiophene) and unsatisfactory naphthalene yields.

Objects of the invention are illustrated in the figure. The drawing illustrates an apparatus for carrying out the invention and a more detailed description follows in the specification.

An object of this invention is to develop a process which will simultaneously yield sulfur free naphthalene of the highest purity, and pure thionaphthene (benzothiophene) as a by-product.

It is a further object of this invention to yield pure naphthalene and pure thionaphthene without the dangers accompanying the sodium melt method.

The problem of obtaining pure naphthalene substantially free of sulfur and pure thionaphthene as a by-product from bituminous coal tar is solved by the conversion of the thionaphthene into its sulfonic acid in the presence of acetic acid anhydride. The mixture of naphthalene and the sulfonic acid derivative of thionaphthene is separated into naphthalene and a thionaphthene sulfonic acid derivative. The thionaphthene sulfonic acid derivative is then converted back into thionaphthene by heating and cleavage of the sulfonic acid group. More particularly, fractional distillation or oxidative purification in the gaseous phase is used to separate a thionaphthene-containing naphthalene fraction from bituminous coal tar. The thionaphthene-containing naphthalene fraction is dissolved in cold benzene (1.8 to 3.0 liters of benzene per 1 kg of naphthalene). Acetic acid anhydride is added to the solution which is run countercurrent in an extracting column with sulfuric acid. The sulfuric acid concentration is about 1 mole $H_2SO_4$ : 1 mole thionaphthene. The acetic acid anhydride concentration is sufficient to bind the free water in the sulfuric acid and water produced by the reaction. In a second extraction column the thionaphthene sulfonic acid derivative-naphthalene-benzene solution is extracted with water. The aqueous phase contains the thionaphthene in its sulfonic acid derivative form. The benzene is separated from the benzene-naphthalene solution and pure naphthalene is distilled off. The remaining aqueous phase is steamed until clear, and the density by concentration is about 1.3. Thionaphthene is liberated from this solution with super-heated steam at about 115° to about 140°.

When oxidative purification of the naphthalene in the gaseous phase is used, a preferred embodiment incorporates the catalyst $SiO_2/Al_2O_3$ (85 : 15) with a carbon priming (content) of 10 to 20%, and preferably of 11 to 17% in a fluidized bed of a separation column.

The starting material of this invention is preferably a de-phenolized thionaphthene-containing naphthalene product, which has been enriched by oxidative purification in the gaseous phase or by distillation. The thionaphthene-containing naphthalene material in a cold inert solvent in the presence of acetic acid anhydride is subjected to sulfuric acid extraction converting the thionaphthene into its sulfonic acid derivative. After extraction, the resulting product undergoes a neutral washing with water and separation from the solvent and is distilled.

The neutral water washing fraction contains the thionaphthene in its sulfonic acid derivative form. Subjecting the thionaphthene sulfonic acid derivative to distillation conditions cleaves the bond of the sulfonic acid group, permitting recovery of pure thionaphthene.

The oxidative purification treatment utilizing the preferred embodiment of an $SiO_2/Al_2O_3$ catalyst, which is also a feature of the present invention, yields a material consisting substantially only of naphthalene and thionaphthene. The process of this invention can yield a naphthalene with a solidification point of 80.30° C and a thionaphthene having a solidification point of 30° C, when this material is employed.

In a preferred embodiment of this invention, a de-phenolized naphthalene fraction, obtained by distillation from bituminous coal tar, having a naphthalene content of about 92 to 96% by weight is subjected to oxidative purification. This is conducted in the gaseous phase with an $SiO_2/Al_2O_3$ (85 : 15) fluidized bed catalyst. The product of the oxidative purification is a naphthalene-thionaphthene product. All other substances are burned during the oxidative purification. In the process according to the invention, a catalyst with extremely high, continued activity for the reaction is obtained when the residual carbon content after regeneration is about 10 to about 20%, preferably about 11 to about 17% of the catalyst. This catalyst, as compared to catalysts known in the art, has the extraordinary advantages of long useful life, uniform naphthalene and thionaphthene content, with no adverse effect on the naphthalene.

In the process according to the invention, a regenerator utilizing air in methods well known in the prior art adjusts the carbon content of circulating catalyst to the ranges of the invention. The circulating catalyst always undergoes this carbon priming prior to being fed into the reactor. This operation takes place in a fluidized bed reactor at temperatures between about 300° and 500° C and preferably at about 400° C.

The naphthalene-thionaphthene material obtained in this manner does not contain other impurities. The thionaphthene-containing naphthalene is dissolved in benzene (1.8 to 3 liters benzene/kg naphthalene) and is treated with sufficient concentrated sulfuric acid to form the sulfonic acid derivative of the thionaphthene. To this mixture, sufficient acetic acid anhydride is added to chemically bond the water present in the sulfuric acid and the water developed during the reaction. The resulting sulfonic acid solution is comprised of about 90% thionaphthene sulfonic acid. The thionaphthene sulfonic acid can be isolated by extraction. The benzene-naphthalene solution is distilled, separating the benzene, leaving a surprisingly pure naphthalene which is absolutely free of thionaphthene and completely stable to light. It has a solidification point of 80.30° C, which corresponds to practically 100% pure naphthalene.

The process is explained in detail according to the accompanying FIGURE.

D1 is a continuous fractional distillation column.

D2 is a continuous benzene distillation column.
D3 is a continuous naphthalene distillation column.
E1 is an extraction column.
E2 is an extraction column.
R1 is a still for distilling off the water.
R2 is a steam distillation apparatus.

In the FIGURE, according to the preferred embodiment of the invention, the benzene-thionaphthene-containing naphthalene solution previously treated with acetic acid anhydride is continuously fed into a pulsating extraction column E1 at points 12 and 13. In addition, a lower sidecut from D1 is injected into the bottom of E1 for processing. Other bottom cuts or top cuts can be removed from D1 for storage or further processing at 22 and 21, respectively. Simultaneously with the feeding operation, the column E1 is being charged with the calculated quantity of concentrated sulfuric acid at point 14, to run countercurrent to the benzene-thionaphthene-containing naphthalene solution. The benzene phase, containing practically the entire sulfonic acid derivative of the thionaphthene formed in E1 reaches the lower part of the second extraction column E2 where water is added as the extracting agent at 15. The washing process yields a completely neutral benzene-naphthalene solution at the head of the column, which is continuously fed to a benzene distilling column D2.

The benzene distilled off from column D2 is recycled and fed into extraction column E1 at point 12 after mixing with a naphthalene and acetic acid anhydride solution. A colored naphthalene is obtained as the sump of D2, which is distilled in D3 to yield a pure colorless naphthalene completely stable to light. The naphthalene is taken off column D3 at point 24. The residue from D3 is drawn off at 25 for further processing or storage.

The acid wash water obtained at the lower end of E2 is united with settled acid portions of E1 and fed into a still R1 at point 16 for concentrating the aqueous phase by distilling off the water. The solution is freed of dissolved naphthalene (by distillation at 26) and concentrated to a density of 1.3 prior to reaching a steam distillation apparatus R2. The sulfonic acid group of the thionaphthene sulfonic acid derivative is cleaved by means of super-heated steam added to the steam distillation apparatus R2 at 18. Thionaphthene removed from R2 at 27 contains 10% naphthalene. The residue from the distillation is discharged at 28. Thionaphthene is obtained by fractional distillation or by partial crystallisation with a solidification point of 30° C which corresponds to a purity of 98%.

A less pure naphthalene is obtained by fractionation of the de-phenolized distillate from a continuous coal tar distillation in a 40 plate column D1. About 10% to about 15% of the initial charge is separated as a first run. This less pure naphthalene contains thionaphthene and other attendant substances such as methylindenes, hydrindene, methyl naphthalenes, and other high boiling compounds in small quantities; it can also be quantitatively desulfurized according to this continuous process. A distilled material from column D1 generally has a solidification point of 78.00° to 79.00° C and a naphthalene content of 92 to 95%.

After withdrawal of the thionaphthene by extractive sulfonation — the remaining contaminants are hardly affected by this low reaction temperature — a sulfur-free naphthalene material having a solidification point of 80.00° to 80.20° C is obtained.

The following are examples of preferred embodiments of the invention.

EXAMPLE 1

Oxidative Purification of Naphthalene 640 parts of naphthalene with a solidification point of 77.25° C and a purity of 95% are guided over 50 parts of a fluid cracking catalyst (LA-LPV of the firm Ketjen) which consists of $SiO_2/Al_2O_3$ in a ratio of 85 : 15 in a fluidized bed reactor at about 400° C. At the same time, 300 liters of air/kg naphthalene are fed into the system. During the feeding-in process, the catalyst is conveyed across a stripper, a dosing worm and a catalyst elevator into a regenerator at a rate of 20 parts/hr.

The activation of the catalyst takes place at about 475° C in the presence of air (2.5 liters of air/part catalyst/hour). The catalyst is again fed to the reactor where a carbon priming of about 10% yields a product which leaves the reactor containing 17% carbon.

Given a residence time of 4.8 to 5.0 secs., a space velocity of 720 to 752 $h^{-1}$ and a flow velocity of 6.9 to 7.2 cm/sec., 576 parts of naphthalene will be produced with a solidification temperature of 79.42° C and a purity of 98.04%. The only impurity in the naphthalene was 1.96% of thionaphthene.

EXAMPLE 2

Production of the Purest Naphthalene and Thionaphthene 10 kg of the naphthalene solution according to Example 1, i.e., a solidification point of 79.42° C and 1.96% thionaphthene as the only impurity, was further processed. The 10 kg of naphthalene was added to 20 liters of benzene and 344 ml of acetic acid anhydride at the lower end of the extraction column E1, and fed within 1 hour into a pulsating extraction column having 40 sieve plates, a diameter of 50m/m, and a length of 4000m/m. Simultaneously 162 ml of concentrated sulfuric acid are dosed in as a heavy phase at the head of the column.

The displacement of the pulsator amounts to 22.7 $cm^3$, with a stroke frequency of 150 strokes/min.

The benzene phase leaving the column reaches a second extraction column (E2) of similar construction in which the sulfonic acids dissolved in the benzene phase are completely washed out with water under the same operating conditions as those in E1.

In this case 11 liters of a strongly acid wash water is accumulated.

After distilling off the benzene and distilling the naphthalene over, 9.4 kg of naphthalene having a solidification point of 80.30° C are obtained.

In order to isolate thionaphthene, the acid washing solution is concentrated until the acid concentrate has a density of 1.3.

Cleavage of the sulfonic acid group is accomplished in a known manner at 125° to 138° C with superheated steam of about 180° C. This yields 120 g of pure thionaphthene having a solidification point of 30° C, corresponding to a purity of 98%.

EXAMPLE 3

Obtaining Sulfur-free Pure Naphthalene 10 kg naphthalene distillate, solidification point 78.15° C, are obtained by fractionation from a de-phenolized naphthalene material having a solidification point of 77.25° C. The dephenolized naphthalene material has small quantities of impurities which include methyl indenes, hydrindene, methyl naphthalenes and other high boiling compounds in addition to 2.4% of thionaphthene. The de-phenolized material is dissolved in 20 liters of benzene and 498 ml of acetic acid anhydride and is fed into a pulsating extraction column as described in Example 2.

At the same time, 198 ml of concentrated sulfuric acid are charged in the column to run countercurrent.

The benzene-naphthalene-thionaphthene sulfonic acid solution is washed with water in a second pulsating column. The benzene is distilled off and naphthalene is distilled over. This yields 9.3 kg of sulfur-free pure naphthalene having a solidification point of 80.13° C.

While we have illustrated and described particular embodiments of our invention, it will be understood that various modifications may be made therein without departing from the spirit of the invention and the scope of the appended claims.

What is claimed is:

1. Process for the preparation of substantially pure naphthalene substantially free of sulfur from bituminous coal tar and for the recovery of thionaphthene as a by-product, said process comprising:
    (a) separating a thionaphthene-containing naphthalene fraction from a dephenolized naphthalene material with a naphthalene content of 92 to 96% by weight obtained by distillation from bituminous coal tar by fractional distillation or oxidative purification in a gaseous phase;
    (b) dissolving said thionaphthene-containing naphthalene fraction in cold benzene to form a solution containing about 1 kg of naphthalene per about 1.8 to about 3.0 l benzene;
    (c) mixing said solution from step (b) with acetic acid anhydride;
    (d) treating the solution resulting from step (c) with concentrated sulfuric acid in an extraction column to convert thionaphthene to a sulfonic acid derivative thereof, wherein flow of said solution is countercurrent to flow of said concentrated sulfuric acid and said concentrated sulfuric acid is employed in an amount of about 1 mole $H_2SO_4$ per 1 mole thionaphthene;
    (e) extracting the solution resulting from step (d) with water in a second extraction column from which an aqueous phase and a benzene solution are obtained;
    (f) distilling the benzene solution from step (e) to remove benzene and recover substantially pure naphthalene;
    (g) concentrating the aqueous phase from step (e) to adjust the density of said phase to about 1.3;
    (h) contacting the concentrated aqueous phase from step (g) with superheated steam at about 115° to about 140° C in order to liberate thionaphthene, wherein said acetic acid anhydride is employed in an amount sufficient to bind reaction water and water in said sulfuric acid.

2. Process according to claim 1 wherein said thionaphthene-containing naphthalene fraction is treated by oxidative purification in a fluidized bed in the presence of an $SiO_2/Al_2O_3$ catalyst (85 : 15 weight ratio) having a carbon content of about 10 to about 20% by weight.

3. Process according to claim 2 in which said carbon content is about 11 to about 17% by weight.

4. Process according to claim 2 in which said carbon content is adjusted in a fluidized bed regenerator in the presence of air at a temperature of about 300° to about 500° C.

5. Process according to claim 4 in which said carbon content is adjusted at about 400° C.

* * * * *